United States Patent [19]

Tomalia

[11] Patent Number: 4,737,550
[45] Date of Patent: Apr. 12, 1988

[54] BRIDGED DENSE STAR POLYMERS

[75] Inventor: Donald A. Tomalia, Midland, Mich.

[73] Assignee: The Dow Chemical Company, Midland, Mich.

[21] Appl. No.: 938,686

[22] Filed: Dec. 8, 1986

Related U.S. Application Data

[63] Continuation-in-part of Ser. No. 755,259, Jul. 15, 1985, Pat. No. 4,631,337, which is a continuation-in-part of Ser. No. 641,807, Aug. 17, 1984, Pat. No. 4,568,737, which is a continuation-in-part of Ser. No. 565,686, Dec. 27, 1983, Pat. No. 4,558,120, which is a continuation-in-part of Ser. No. 456,226, Jan. 7, 1983, Pat. No. 4,507,466.

[51] Int. Cl.$^4$ .............................................. C08G 83/00
[52] U.S. Cl. ..................................... 525/418; 525/419; 525/420; 525/540; 528/271; 528/310; 528/332; 528/350; 528/363; 528/373; 528/374; 528/397; 528/403; 528/405; 528/422; 528/425
[58] Field of Search ............. 525/418, 419, 420, 540; 528/310, 332, 363, 271, 350, 373, 374, 425, 422, 397, 403, 405

[56] References Cited

U.S. PATENT DOCUMENTS 4,631,337  12/1986  Tomalia et al. ..................... 528/423

*Primary Examiner*—Harold D. Anderson

[57] ABSTRACT

Bridged dense star polymers having terminal group densities greater than conventional extended star polymers exhibit greater and more uniform reactivity than their corresponding conventional star polymers. For example, a third generation, hydroxy-terminated polyether dense star polymer can be prepared from pentaerythrityltetrabromide and 4-hydroxymethyl-2,6,7-trioxabicyclo[2.2.2]-octane which has a molecular volume less than 80 percent of the volume of a conventional extended star polymer made from similar materials. This dense star polymer can then be bridged by reacting it with a suitable difunctional reactant such as toluene diisocyanate. Such polymers of dense star polymers are useful as demulsifiers for oil/water emulsions, wet strength agents in the manufacture of paper, proton scavengers, calibration standards for electron microscopy, and agents for modifying viscosity in aqueous formulations such as paints.

32 Claims, No Drawings

BRIDGED DENSE STAR POLYMERS

CROSS-REFERENCE TO RELATED APPLICATIONS

This application is a continuation-in-part of application Ser. No. 755,259, filed on July 15, 1985, now U.S. Pat. No. 4,631,337, which is a continuation-in-part of application Ser. No. 641,807, filed on Aug. 17, 1984, now U.S. Pat. No. 4,568,737, which is a continuation-in-part of application Ser. No. 565,686, filed on Dec. 27, 1983, now U.S. Pat. No. 4,558,120, which is a continuation-in-part of application Ser. No. 456,226, filed on Jan. 7, 1983, now U.S. Pat. No. 4,507,466.

BACKGROUND OF THE INVENTION

This invention relates to a novel class of branched polymers containing dendritic branches having functional groups uniformly distributed on the periphery of such branches. This invention also relates to processes for preparing such polymers as well as applications therefore.

Organic polymers are generally classified in a structural sense as either linear or branched. In the case of linear polymers, the repeating units (often called mers) are divalent and are connected one to another in a linear sequence. In the case of branched polymers, at least some of the mers possess a valency greater than 2 such that the mers are connected in a nonlinear sequence. The term "branching" usually implies that the individual molecular units of the branches are discrete from the polymer backbone, yet have the same chemical constitution as the polymer backbone. Thus, regularly repeating side groups which are inherent in the monomer structure and/or are of different chemical constitution than the polymer backbone are not considered as branches, e.g., dependent methyl groups of linear polypropylene. To produce a branched polymer, it is necessary to employ an initiator, a monomer, or both that possess at least three moieties that function in the polymerization reaction. Such monomer or initiators are often called polyfunctional. The simplest branched polymers are the chain branched polymers wherein a linear backbone bears one or more essentially linear pendant groups. This simple form of branching, often called comb branching, may be regular wherein the branches are uniformly and regularly distributed on the polymer backbone or irregular wherein the branches are distributed in nonuniform or random fashion on the polymer backbone. See T. A. Orofino, Polymer, 2, 295–314 (1961). An example of regular comb branching is a comb branched polystyrene as described by T. Altores et al. in *J. Polymer Sci., Part A*, Vol. 3, 4131–4151 (1965) and an example of irregular comb branching is illustrated by graft copolymers as described by Sorenson et al. in "Preparative Methods of Polymer Chemistry", 2nd Ed., Interscience Publishers, 213–214 (1968).

Another type of branching is exemplified by cross-linked or network polymers wherein the polymer chains are connected via tetravalent compounds, e.g., polystyrene molecules bridged or cross-linked with divinylbenzene. In this type of branching, many of the individual branches are not linear in that each branch may itself contain groups pendant from a linear chain. More importantly in network branching, each polymer macromolecule (backbone) is cross-linked at two or more sites to two other polymer macromolecules. Also the chemical constitution of the cross-linkages may vary from that of the polymer macromolecules. In this so-called cross-linked or network branched polymer, the various branches or cross-linkages may be structurally similar (called regular cross-linked) or they may be structurally dissimilar (called irregularly cross-linked). An example of regular cross-linked polymers is a ladder-type poly(phenylsilsesquinone) as described by Sorenson et al., supra, at page 390. The foregoing and other types of branched polymers are described by H. G. Elias in *Macromolecules*, Vol. I, Plenum Press, New York (1977).

More recently, there have been developed polymers having so-called star structured branching wherein the individual branches radiate out from a nucleus and there are at least 3 branches per nucleus. Such star branched polymers are illustrated by the polyquaternary compositions described in U.S. Pat. Nos. 4,036,808 and 4,102,827. Star branched polymers prepared from olefins and unsaturated acids are described in U.S. Pat. No. 4,141,847. The star branched polymers offer several advantages over polymers having other types of branching. For example, it is found that the star branched polymers may exhibit higher concentrations of functional groups thus making them more active for their intended purpose. In addition, such star branched polymers are often less sensitive to degradation by shearing which is a very useful property in formulations such as paints, in enhanced oil recovery and other viscosity applications. Additionally, the star branched polymers have relatively low intrinsic viscosities even at high molecular weight.

While the star branched polymers offer many of the aforementioned advantages over polymers having more conventional branching, it is highly desirable to provide polymers which exhibit even greater concentrations of functional groups per unit volume of the polymer macromolecule as well as a more uniform distribution of such functional groups in the exterior regions of the macromolecule. In addition, it is often desirable to provide polymers having macromolecular configurations that are more spheroidal and compact than are the star branched polymers.

SUMMARY OF THE INVENTION

In its broadest aspect, this invention is a bridged dense star polymer wherein the dense star polymer prior to bridging has at least one branch (hereinafter called a core branch) emanating from a core, said branch having at least one terminal group provided that (1) the ratio of terminal groups to the core branches is more than one, preferably two or greater, (2) the density of terminal groups per unit volume in the dense star polymer is at least 1.5 times that of an extended conventional star polymer having similar core and monomeric moieties and a comparable molecular weight and number of core branches, each of such branches of the extended conventional star polymer bearing only one terminal group, and (3) a molecular volume that is no more than about 80 percent of the molecular volume of said extended conventional star polymer as determined by dimensional studies using scaled Corey-Pauling molecular models.

For purposes of this invention, the term "bridged" as it modifies "dense star polymer" means a dense star polymer in which a dense star polymer molecule is covalently bonded to at least one other dense star polymer molecule. The term "dense" as it modifies "star polymer" means that it has a smaller molecular volume than an extended conventional star polymer having the same molecular weight. The extended conventional star polymer which is used as the base for comparison with the dense star polymer is one that has the same molecular weight, same core and monomeric components and same number of core branches as the dense star polymer. By "extended" it is meant that the individual branches of the conventional star polymer are extended or stretched to their maximum length, e.g., as such branches exist when the star polymer is completely solvated in an ideal solvent for the star polymer. In addition while the number of terminal groups is greater for the dense star polymer molecule than in the conventional star polymer molecule, the chemical structure of the terminal groups is the same.

In a somewhat more limited and preferred aspect, this invention is a bridged dense star polymer having a novel ordered star branched structure (herein called starburst structure). Hereinafter this bridged polymer having a starburst structure is called a polydendrimer or bridged dendrimer. A "dendrimer" is a polymer having a polyvalent core that is covalently bonded to at least two ordered dendritic (tree-like) branches which extend through at least two generations. As an illustration, an ordered second generation dendritic branch is depicted by the following configuration:

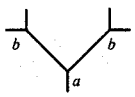

wherein "a" represents the first generation and "b" represents the second generation. An ordered, third generation dendritic branch is depicted by the following configuration:

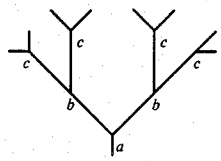

wherein "a" and "b" represent the first and second generation, respectively, and "c" represents the third generation. A primary characteristic of the ordered dendritic branch which distinguishes it from conventional branches of conventional polymers is the uniform or essentially symmetrical character of the branches as is shown in the foregoing illustrations. In addition, with each new generation, the number of terminal groups on the dendritic branch is an exact multiple of the number of terminal groups in the previous generation.

Another aspect of the present invention is a process for preparing the bridged dense star polymers of the present invention.

Such bridged dense star polymers are useful in such applications as demulsifiers for oil/water emulsions, wet strength agents in the manufacture of paper, size selective membranes, high efficiency proton scavengers, agents for calibrating sub-micron apertures and calibration standards for electron microscopy, agents for modifying viscosity in aqueous formulations such as paints, and the like. For example, in a demulsification method, an emulsion of oil and water is contacted with a demulsifying amount of the bridged dense star polymer under conditions sufficient to cause phase separation.

DETAILED DESCRIPTION OF ILLUSTRATIVE EMBODIMENTS

In the dense star polymers which are bridged in the present invention, the core is covalently bonded to at least one core branch, preferably at least two, most preferably at least three, core branches with each core branch having a calculated length of at least 3 Angstrom units (A), preferably at least 4 A, most preferably at least 6 A. These polymers preferably have an average of at least 2, more preferably at least 3 and most preferably at least 4 terminal groups per polymer molecule. Preferably, the core branches have a dendritic character, most preferably an ordered dendritic character as defined hereinafter.

These bridged dense star polymers preferably have projected two-dimensional molecular diameters in the range from about 12 to about 2000 Angstrom units (A), more preferably from about 25 A to about 500 A and most preferably from about 50 A to about 250 A. For the purpose of this invention, a two-dimensional molecular diameter is determined by the following electron microscopic method. First, the terminal groups of dendrimers are connected to anionic moieties (e.g., by hydrolysis of the terminal ester moieties of polyamidoamine dendrimer in half generation state). The anionic dendrimer molecules are then neutralized with stoichiometric amounts of alkali metal hydroxide. A dilute aqueous solution (e.g., about 0.5 weight percent of the neutralized dendrimer in water) of the dendrimer is placed on a beryllium grid (~1.5 millimeter diameter puddle) and allowed to evaporate. The dendrimer often exhibits dendritic-like crystalline growth during the evaporation process. The diameter of the dry dendrimer molecules in two-dimensional state are then measured by electron microscopy and found to correspond closely, e.g., within 15 percent, to the diameters predicted by scaled Corey-Pauling molecular models. Such measurements are readily made using a *JEM*-1200 *EX Electron Microscope* sold by JEOL Corporation using CTEM techniques on a beryllium grid coated with 50 A carbon.

These bridged dense star polymers preferably have three-dimensional molecular diameters in the range from about 6 to about 1000, more preferably from about 10 to about 250, most preferably from about 25 to about 125 Angstrom units. For the purposes of this invention, a three-dimensional molecular diameter is determined by calculating hydrodynamic diameters using the following Hester-Mitchell relationship, R. D. Hester et al., *J. Poly Sci.*, Vol. 18, p. 1727 (1980).

$$d = \left\{ \left( \frac{240}{\pi N} \right)^{\frac{1}{2}} \{M(\eta)\}^{\frac{1}{3}} \right\} 10^8$$

wherein d is the hydrodynamic diameter in Angstrom units; N is $6.02 \times 10^{23}$; M is number average molecular weight of the dendrimer; $\pi$ is 3.14; and $\eta$ is intrinsic viscosity of the dense star polymer in deciliters per gram at 25° C.

In preferred dense star polymers (e.g., dendrimers), the terminal groups are functional groups that are sufficiently reactive to undergo addition or substitution reactions, particularly reactions that permit bridging of the dendrimers. Examples of such functional groups include amino, hydroxy, mercapto, carboxy, alkenyl, allyl, vinyl, amido, halo, urea, oxiranyl, aziridinyl, oxazolinyl, imidazolinyl, sulfonato, phosphonato, isocyanato and isothiocyanato. The dense star polymers differ from conventional star or star-branched polymers in that the dense star polymers have a greater concentration of terminal groups per unit of molecular volume than do conventional extended star polymers having an equivalent number of core branches and an equivalent core branch length. Thus, the density of terminal groups per unit volume in the dense star polymer is at least about 1.5 times the density of terminal groups in the conventional extended star polymer, preferably at least 5 times, more preferably at least 10 times, most preferably from about 15 to about 50 times. The ratio of terminal groups per core branch in the dense polymer is preferably at least 2, more preferably at least 3, most preferably from about 4 to about 1024. Preferably, for a given polymer molecular weight, the molecular volume of the dense star polymer is less than 80 volume percent, more preferably from about 16 to about 60, most preferably from about 7 to about 50 volume percent of the molecular volume of the conventional extended star polymer.

In the preferred polyether dense star polymers, the density of terminal functional moieties, usually hydroxy, in the polymer is readily expressed as the molar ratio of terminal functional moieties to the total ether moieties. In such polymers this molar ratio of terminal groups to ether groups is preferably from about 0.3:1 to about 4:1, more preferably from about 0.7:1 to about 3:1, most preferably from about 1:1 to about 2:1.

The preferred dendrimers are characterized as having a polyvalent core that is covalently bonded to at least two ordered dendritic branches which extend through at least two generations. Such ordered branching can be illustrated by the following sequence wherein G indicates the number of generations:

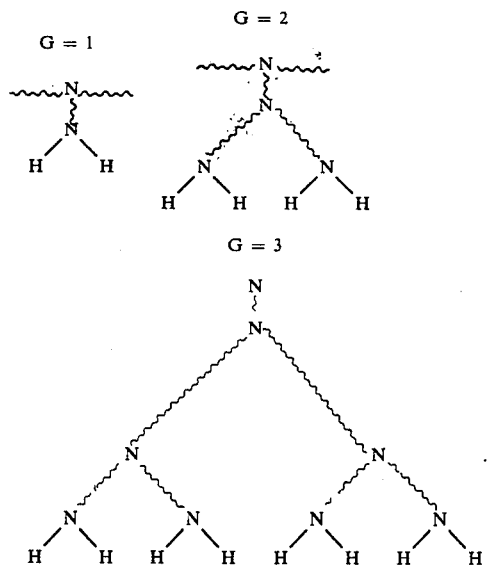

Mathematically, the relationship between the number of terminal groups on a dendritic branch and the number of generations of the branch can be represented as follows:

# of terminal groups=$(N_r{}^G/2)$ per dendritic branch wherein G is the number of generations and $N_r$ is the repeating unit multiplicity which is at least 2 as in the case of amines. The total number of terminal groups in the dendrimer is determined by the following:

# of terminal groups=$(N_c N_r{}^G/2)$ per dendrimer wherein G and $N_r$ are as defined before and $N_c$ represents the valency (often called core functionality) of the core compound. Accordingly, the dendrimers of the present invention can be represented in its component parts as follows:

$$(\text{Core})\left\{(\text{Repeat Unit})\frac{N_r{}^G - 1}{N_r - 1} \quad \substack{\text{Terminal} \\ \text{Moiety}} \; N_r{}^G \right\}_{N_c}$$

wherein the Core, Terminal Moiety, G and $N_c$ are as defined before and the Repeat Unit has a valency or functionality of $N_r+1$ wherein $N_r$ is as defined before.

A copolymeric dendrimer which is a preferred dendrimer for the purposes of this invention is a unique compound constructed of polyfunctional monomer units in a highly branched (dendritic) array. The dendrimer molecule is prepared from a polyfunctional initiator unit (core compound), polyfunctional repeating units and terminal units which may be the same or different from the repeating units. The core compound is represented by the formula ⓘ$(Z^c)_{Nc}$ wherein ⓘ represents the core, $Z^c$ represents the functional groups bonded to I and Nc represents the core functionality which is preferably 2 or more, most preferably 3 or more. Thus, the dendrimer molecule comprises a polyfunctional core, ⓘ, bonded to a number (Nc) of functional groups, $Z^c$, each of which is connected to the monofunctional tail of a repeating unit, $X^1Y^1(Z^1)_{N1}$, of the first generation and each of the Z groups of the repeating unit of one generation is bonded to a monofunctional tail of a repeating unit of the next generation until the terminal generation is reached. In the dendrimer molecule, the repeating units are the same within a single generation, but may differ from generation to generation. In the repeating unit, $X^1Y^1(Z^1)_{N1}$, $X^1$ represents the monofunctional tail of the first generation repeating unit, $Y^1$ represents the moiety constituting the first generation, $Z^1$ represents the functional group of the polyfunctional head of the repeating unit of the first generation and may be the same as or different from the functional groups of the core compound, I $(Z^c)_{Nc}$, or other generations; and $N^1$ is a number of 2 or more, most preferably 2, 3 or 4, which represents the multiplicity of the polyfunctional head of the repeating unit in the first generation. Generically, the repeating unit is represented by the formula $X^i Y^i(Z^i)_{Ni}$ wherein "i" represents the particular generation from the first to the t-1 generation. Thus, in the preferred dendrimer molecule, each $Z^1$ of the first generation repeating unit is connected to an $X^2$ of a repeating unit of the second generation and so on through the generations such that each $Z^i$ group for a repeating unit $X^i Y^i(Z^i)_{Ni}$ in generation number "i" is connected to the tail $(X^{i+1})$ of the repeating unit of the generation number "i+1". The final or terminal of a preferred dendrimer molecule comprises terminal units, $X^t Y^t(Z^t)_{Nt}$ wherein t represents terminal generation and $X^t$, $Y^t$, $Z^t$ and $N^t$ may be the same as or different from $X^i$, $Y^i$, $Z^i$ and $N^i$ except that there is no succeeding generation connected to the $Z^t$ groups and $N^t$ may be less than two, e.g., zero or one. Therefore the preferred dendrimer has a molecular formula represented by $$(\textcircled{I})(Z^c)_{N_c}\left[(X^iY^i(Z^i)_{Ni})N_c\pi N^n \begin{matrix} i-1 \\ \\ n \text{ is } 1 \end{matrix}\right](X^tY^t(Z^t)_{Nt})N_c\pi N^n. \begin{matrix} t-1 \\ \\ n \text{ is } 1 \end{matrix}$$

where $i$ is $1$ to $t-1$ wherein the symbols are as previously defined. The $\pi$ function is the product of all the values between its defined limits. Thus $$\pi_{n=1}^{i-1} N^n = (N^1)(N^2)(N^3)\ldots(N^{i-2})(N^{i-1})$$

which is the number of repeat units, $X^iY^i(Z^i)_{Ni}$, comprising the ith generation of one dendritic branch and when i is 1, then $$\pi^0_{n=1} = 1.$$

In copolymeric dendrimers, the repeat unit for one generation differs from the repeat unit in at least one other generation. The preferred dendrimers are very symmetrical as illustrated in structural formulas described hereinafter. Preferred dendrimers may be converted to functionalized dendrimers by contact with another reagent. For example, conversion of hydroxyl in the terminal generation to ester by reaction with an acid chloride gives an ester terminally functionalized dendrimer. This functionalization need not be carried out to the theoretical maximum as defined by the number of available functional groups and, thus, a functionalized dendrimer may not have high symmetry or a precisely defined molecular formula as is the case with the present dendrimer.

The preferred bridged dendrimers have a molecular formula represented by $$\left\{(\textcircled{I})(Z)^c{}_{N_c}\left\{(X^iY^i(Z^i)_{Ni})N_c\pi N^n \begin{matrix} i-1 \\ \\ n \text{ is } 1 \end{matrix}\right\}(X^tY^t(Z)^t{}_{Nt})N_c\pi N- L(X^tY^t(\Omega)^t)_L \begin{matrix} t-1 \\ \\ n \text{ is } 1 \end{matrix}\right\}_V$$

where $i$ is to $t-1$ wherein the various symbols are as defined hereinbefore and wherein $\Omega$ is the linking group formed from $Z^t$, L is the number of terminal groups ($Z^t$) converted to bridging links ($\Omega$), and V is the degree of polymerization which is 2 or greater.

An illustration of a functionally active dendrimer of a ternary or trivalent core which has three ordered, second generation dendritic branches as depicted by the following configuration:

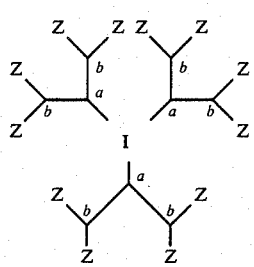

wherein $\textcircled{I}$ is a trivalent core atom or molecule having a covalent bond with each of the three dendritic branches, Z is a terminal moiety and "a" and "b" are as defined hereinbefore. An example of such a ternary dendrimer is polyether represented by the following structural formula:

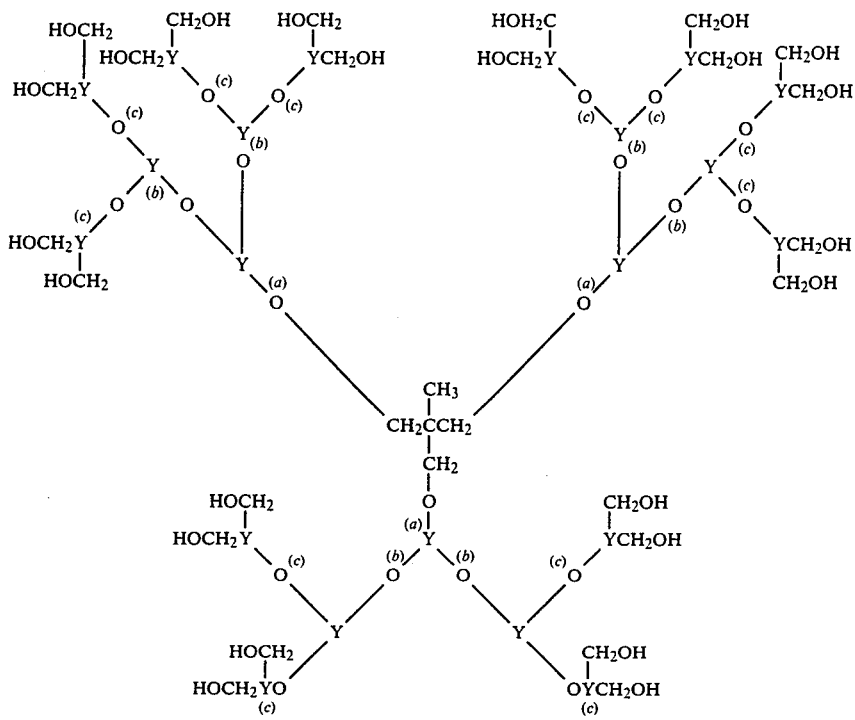

wherein Y represents a trivalent moiety such as —CH(CH$_2$—)$_2$,

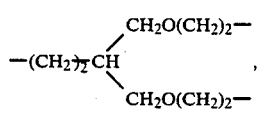

—CH$_2$CHCH$_2$—, or —C(CH$_3$)(CH$_2$—)$_2$ and "a" and "b" indicate first and second generations, respectively. Also, Y may be a tetravalent moiety such as —CH$_2$C(CH$_2$—)$_3$. In these two illustrations, $N_c$ is 3 and $N_r$ is 2. In the latter of the two illustrations, the Repeat Unit is YO. The number of terminal groups (Z) can be determined as a function of generation according to the following equation: # of Z = $N_c N_r^G$. While the foregoing configuration and formula illustrate a trivalent core, the core atom or molecule may be any monovalent or monofunctional moiety or any polyvalent or polyfunctional moiety, preferably a polyvalent or polyfunctional moiety having from 2 to about 2300 valence bonds or functional sites available for bonding with the dendritic branches, most preferably from about 2 to about 200 valence bonds or functional sites. In cases wherein the core is a monovalent or monofunctional moiety, the dense star has only one core branch and must be compared with a linear polymer in order to determine appropriate terminal group density and molecular volume. Accordingly, this dense star must have at least 2 generations in order to exhibit the desired density of terminal groups. Also, Y may be any other trivalent or tetravalent organic moiety such as aryltriyl or aryltetrayl, and the like, with the depicted alkyltriyl moiety being the most preferred. It is further understood that Y may be a polyvalent moiety such as triyls, tetrayls and other poly-yls of aliphatic and aromatic hydrocarbons, e.g., and the like.

In addition to hydroxy, the terminal groups of the dendrimer may be any functionally active moiety that can be used to propagate the dendritic branch to the next generation. Examples of such other moieties include alkoxycarbonyl, amino, alkenyl, aziridinyl, oxazolinyl, haloalkyl, oxiranyl, isothiocyanato and isocyanato, with hydroxy or amine moieties being preferred. While the dendrimers preferably have dendritic branches having 2 to 6 generations, dendrimers having dendritic branches up to 12 generations are suitably made and employed in the practice of this invention.

More preferably, the polyether dendrimers are represented by the formula:

I {(ZB—Z—B—(ZR)$_2$)$_2$}$_n$ wherein Ⓘ is an n-valent core derived from a nucleophilic compound, B is a trivalent moiety capable of linking oxy moieties, n is an integer of 3 or more corresponding to the number of the core branches, Z is oxygen or sulfur and R is hydrogen, alkyl, aryl, alkylaryl, hydroxyalkyl, mercapto alkyl, amine alkyl, acyl and the like wherein each generation is represented by ZB. Also, B may be tetravalent, e.g., —B(ZR)$_3$. More preferably A is a core such as

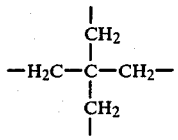

or

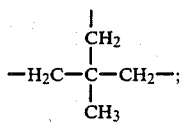

R is hydrogen, methyl, benzyl or aryl; B is alkylene, alkyleneoxyalkylene, polyalkyleneoxyalkylene, arylene, or alkyleneoxyarylene, most preferably an alkylene such as ethylene propylene; and n is an integer from 3 to 2000, more preferably from 3 to 1000, most preferably from 3 to 125.

The dense star polymers are readily prepared by reacting a compound capable of generating a polyvalent core with a compound or compounds which causes propagation of dendritic branches from the core. In one method of preparing these dendrimers (herein called the successive excess reactant method and described in detail in U.S. Pat. No. 4,587,329 which detailed description is hereby incorporated by reference), it is essential to maintain an excess of coreactant to reactive moieties in the terminal groups in the core, core adduct or subsequent adducts and dendrimers in order to prevent crosslinking and to maintain the ordered character of the dendritic branches. In general, this excess of coreactant to reactive moieties in the terminal groups is from about 2:1 to about 1000:1, preferably from about 3:1 to about 120:1 on a molar basis.

Alternatively, the compound capable of generating a polyvalent core, W(X)$_n$, wherein W is the polyvalent core atom and is covalently bonded to nX reactive terminal groups (n≧2), is reacted with a partially protected multifunctional reagent, T(U) Ⓥ $_m$, wherein U represents a multivalent moiety covalently bonded to m Ⓥ protected moieties (m≧2), and to one T, a moiety capable of reacting with X to form W[(X'-T')U Ⓥ $_m$]$_n$, wherein X' and T' represent the residue of reaction between X and T. This first generation compound is then subjected to activation conditions whereby the Ⓥ moieties are made reactive (deprotected) and reacted with the partially protected multifunctional reagent, T-U- Ⓥ $_m$, to form the second generation protected dendrimer, W[(X'-T')UV$_m$T'-U Ⓥ $_m$]$_n$. This protected dendrimer can be activated and reacted again in a similar manner to provide the third generation protected dendrimer. This method is called the partially protected reactant method and is described in detail in U.S. Pat. No. 4,587,329 which detailed description is hereby incorporated by reference.

In either of the foregoing methods of dendrimer preparation, water or hydrogen sulfide may be employed as nucleophilic cores for the production of binary dendrimers. Examples of other nucleophilic core compounds include phosphine, polyalkylene polyamines such as diethylenetriamine, triethylenetetramine, tetraethylenepentamine and both linear and branched polyethyleneimine; primary amines such as methylamine, hydroxyethylamine, octadecylamine and polymethylenediamines such as hexamethylenediamine; polyaminoalkylarenes such as 1,3,5-tris(aminomethyl)-benzene; tris(aminoalkyl)amines such as tris(aminoethyl)amine; heterocyclic amines such as imidazolines and piperidines; and various other amines such as hydroxyethyaminoethylamine, mercaptoethylamine, morpholine, piperazine, amino derivatives of polyvinylbenzyl chloride and other benzylic polyamines such as tris(1,3,5-aminomethyl)benzene. Other suitable nucleophilic cores include polyols such as the aforementioned pentaerythritol, ethylene glycol and polyalkylene polyols such as polyethylene glycol and polypropylene glycol; 1,2-dimercaptoethane and polyalkylene polymercaptans; thiophenols, and phenols. Of the core compounds, ammonia and the polyalkylene polyamines are preferred for the preparation of polyamidoamine dendrimers by the successive excess reactant method and the polyols are preferred for the preparation of polyether dendrimers by the partially protected reactant method.

Examples of coreactant materials used to react with the nucleophilic core compounds include α,β-ethylenically unsaturated carboxylic esters and amides such as methyl acrylate, ethyl acrylate, acrylonitrile, methyl itaconate, dimethyl fumarates, maleic anhydride, acrylamide, as well as esters, acids and nitriles containing an acrylyl moiety, with methyl acrylate being the preferred coreactant material. In general other preferred unsaturated reactants are volatile or otherwise readily removed from the core/coreactant reaction products without deleteriously affecting the reaction product.

Examples of the second coreactant materials used to react with the adduct of the nucleophilic core and the first coreactant include various polyamines such as alkylene polyamines and polyalkylene polyamines such as ethylenediamine and diethylenetriamine; benzylic polyamines such as tris(1,3,5-aminomethyl)benzene; alkanolamines such as ethanolamine; and aziridine and derivatives thereof such as N-aminoethyl aziridine. Of these second coreactant materials, the volatile polyamines such as ethylenediamine and diethylenetriamine are preferred, with ethylenediamine being especially preferred.

Alternatively, the dendrimers can be prepared by reacting an electrophilic core such as a polyester with a coreactant such as a polyamine to form a core adduct which is then reacted with a suitable second coreactant such as an unsaturated ester to form the first generation polyamidoamine. Thereafter, this first generation product is reacted with a suitable third coreactant such as polyamine and then with the second coreactant such as unsaturated ester to form the desired second generation dendrimer. Examples of suitable electrophilic cores include the $C_1$–$C_4$ alkyl esters of various polycarboxylic acids such as benzene tricarboxylic acid, oxalic acid, terphthalic acid and various other carboxylic acids represented by the formula:

wherein Y is hydrocarbyl or a hydrocarbon polyl wherein the hydrocarbon radical is alkyl, aryl, cycloalkyl, alkylene, arylene, cycloalkylene, and corresponding trivalent, tetravalent, pentavalent and hexavalent radicals of such hydrocarbons; and P is a whole number from 1 to 6. Other suitable electrophilic core compounds include polyhalohydrocarbons such as polyhaloalkanes, e.g., 1,1,1-tris(chloromethyl)ethane, tetrakis(bromomethyl)methane, and tris(bromomethyl)hydroxymethyl methane; and polyhaloalkylarenes, e.g., 1,3,5-tris(chloromethyl)-2,4,6-trimethyl benzene, hexakis(bromomethyl)benzene and 1,2,4,5-tetrakis(bromomethyl)benzene. Preferred electrophilic cores include poly(methyl acrylates), poly(acryloyl chloride), poly(methacryloyl chloride), alkyl acrylate/alkyl methacrylate copolymers, polymers of alkyl fumarates, and polymers of alkyl itaconates. Of the electrophilic cores, alkyl acrylate/alkyl methacrylate copolymers and alkyl acrylate/alkyl itaconate copolymers are most preferred.

Suitable first coreactants for reaction with the electrophilic core include polyalkylene polyamines such as ethylenediamine, diethylenetriamine, triethylenetetramine and other polyamines represented by the formula:

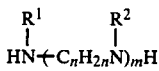

wherein $R^1$ and $R^2$ independently represent hydrogen or an alkyl, preferably $C_1$–$C_4$ alkyl, hydroxyalkyl, cyanoalkyl, or amido; n is at least 2 and preferably 2 to 6 and m is 2 to 100, preferably 2 to 5. Examples of suitable second coreactants to be used in preparing dendrimers from electrophilic cores include alkyl esters of ethylenically unsaturated carboxylic acids such as methyl acrylate, methyl methacrylate, ethyl acrylate and the like. Examples of suitable third coreactants are those illustrated for the first coreactant.

Thus prepared, the dense star polymers can be reacted with a wide variety of compounds to produce polyfunctional compounds having the unique characteristics that are attributable to the structure of the dendrimer. For example, a dendrimer having terminal amine moieties may be reacted with an unsaturated nitrile to yield a polynitrile (nitrile-terminated) dendrimer. Alternatively, a polyamine dendrimer may be reacted with (1) an α,β-ethylenically unsaturated amide to form a polyamide (amide-terminated) dendrimer, (2) an α,β-ethylenically unsaturated ester to form a polyester (ester-terminated) dendrimer, (3) an oxirane to yield a polyol (hydroxy-terminated) dendrimer, or (4) an ethylenically unsaturated sulfide to yield a polymercapto (thiol-terminated) dendrimer. The polyether dendrimer having terminal hydroxyl moieties may be reacted with carboxylic acids to give an ester-terminated dendrimer, with alcohol or alkyl halide to form an ether-terminated dendrimer, with isocyanate to form a urethane-terminated dendrimer, with thionyl chloride to form a chloride-terminated dendrimer, and with tosylate to form a tosyl-terminated dendrimer.

The bridged dense star polymers of this invention are those polymers comprising at least two dense star polymer molecules which are covalently bonded together. Preferably such molecules are bonded through the terminal groups of the dense star polymer molecules.

In certain preferred embodiments, the bridged dense star polymer of the present invention, the dense star prior to bridging has (1) at least 2 core branches per core, (2) a terminal group density at least 5 times that of the corresponding conventional star polymer, and (3) a molecular volume that is equal to or less than 50 percent of the volume of the conventional star polymer.

In another preferred embodiment, the core of the bridged dense star polymers are derived from a core compound having a plurality of active hydrogens capable of undergoing a Michael's addition reaction with an ethylenically unsaturated group.

In yet another preferred embodiment of the present invention, the bridged dense star polymer of the present invention is a dendrimer covalently bridged to at least one other dendrimer through at least one terminal group of each dendrimer, wherein each dendrimer has a polyvalent core that is covalently bonded to at least 1 ordered dendritic branch which extends to two generations such that each dendritic branch has at least four terminal groups and a symmetrical structure.

The bridged dense star polymers of the present invention can be prepared by any suitable process. Such suitable processes may include reactions of condensation, addition utilizing a radical mechanism or, addition utilizing an ionic mechanism as described in *Preparative methods of Polymer Chemistry*, 2nd Edition, W. R. Sorenson and T. W. Campbell, Interscience Publishers, New York (1968); whose preparative teachings are incorporated herein by reference.

In one process for preparation of the bridged dense star polymers, a dense star polymer (dendrimer) having nucleophilic terminal groups is reacted with dense star polymers having electrophilic terminal groups under conditions sufficient to cause reaction and formation of covalent bridges (bonds) between the dense star molecules. Representative nucleophilic terminal groups which are suitable for reaction with an electrophilic terminal group include, but are not limited to amino, mercapto, carboxyl, hydroxyl or malonyl acetylenyl and acetoacetic acid esters, preferably amino, hydroxyl and mercapto, most preferably carboxyl and amino. Representative electrophilic groups suitable for reaction with the nucleophilic group include but are not limited to esters, Michael receptor activated olefin, oxirane, aziridinyl, anhydride, allylic, benzylic halide, acid halide, ammonium salt or sulfonium salt, preferably the activated halides and esters. Where the electrophilic group is a carboxy ester, representative esters include but are not limited to tosylate, mesylate or triflate.

Alternatively, the terminal groups of the dense star polymers may be olefinic and the dense star molecules can be bridged by vinyl polymerization of the olefinic moieties, e.g., via free radical polymerication. Such olefinic moieties are preferably those represented by the formula

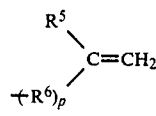

wherein $R^5$ is alkyl, aryl or hydrogen; p is one or zero; and $R^6$ is arylene or a divalent organic moiety such as, e.g.,

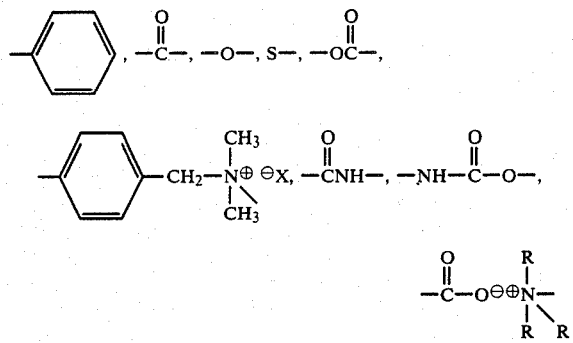

wherein X=Cl, Br or I. Initiation of polymerization can be by ionic or free radical means as is well-known in the art.

These various processes are schematically illustrated in Table I for preparing the bridged dense star polymers or dendrimers of the present invention.

group (ET) to yield a covalently bridged dense star polymer or dendrimer product of Formula I. For example, an amine-terminated dendrimer can be reacted with an ester-terminated dendrimer to covalently bridge the two dendrimers through a covalent amide bridge. Similarly, the wavy lines ($\fallingdotseq$) connected to dendrimers $D^1$ and $D^2$ indicated that bridged dendrimers of Formula I can be further polymerized with other dendrimers, forming even larger bridged dense star polymers or dendrimers.

In Preparation No. 2, dendrimers $D^1$ and $D^2$ having terminal nucleophilic groups can be contacted with a third dendrimer ($D^3$) having electrophilic terminal groups, to yield a bridged dense star polymer or bridged dendrimer of Formula II. The bridged dendrimers of Formula II can be polymerized further to yield even larger bridged dense star polymers or dendrimers.

In Preparation No. 3, dendrimers having a nucleophilic terminal group are contacted with electrophilic reagent $E^1n_1RE^2n_2$, defined hereinbelow, to yield a dense star polymer product or bridged dendrimer of Formula III. The elecrophilic reagent is defined as $E^1n_1QE^2n_2$ wherein $E^1$ and $E^2$ independently represent electrophilic groups; $n_1$ and $n_2$ independently represent integers from 1 to 10; and Q represents arylene and alkylene moieties. Bridged dendrimers of Formula III can be polymerized with other dendrimers to form even larger bridged dense star polymers or dendrimers.

TABLE I

| PREPARATION NUMBER | REACTION MECHANISM | DENSE STAR POLYMER PRODUCT | FORMULA NUMBER |
|---|---|---|---|
| 1 | D¹—NT + D²—ET → | D¹—NT≈ET—D² ↑ Covalent Bridge | (I) |
| 2 | D¹—NT + ET—D³—ET + NT—D² → | D¹—NT—ET—D³—ET—NT—D² | (II) |
| 3 | D¹—NT + D²—NT + $E_{n1}QE_{n2}$ → | D¹—NT—$E_{n1}QE_{n2}$—NT—D² | (III) |
| 4 | D¹—ET + D²—ET + $N^1n^1QN^2n^2$ → | D¹—ET—$N^1n^1QN^2n^2$—ET—D² | (IV) |
| 5 | D¹—ET + NT—D³—NT + ET—D² → | D¹—ET—NT—D³—NT—ET—D² | (V) |
| 6 | D¹—OT + IT—D² → | D¹—OT—IT—D² | (VI) |
| 7 | D¹—OT + CM + IT—D² → | D¹—OT—CM—CT—D² | (VII) |

In Preparation No. 1 shown in Table I, a condensation reaction, dendrimer ($D^1$) having at least one nucleophilic terminal group (NT) is contacted with a second dendrimer ($D^2$) having one electrophilic terminal In Preparation No. 4 which represents a condensation reaction, dendrimers having electriphilic terminal groups can be contacted with a nucleophilic reagent $N^1n_1QN^2n_2$ to yield dense star polymer or bridged dendrimer of Formula IV. The nucleophilic reagent is defined as $N^1n_1QN^2n_2$ wherein $N^1$ and $N^2$ independently represent nucleophilic groups; $n_1$ and $n_2$ independently represent integers from 1 to 10; and Q represents arylene and alkylene moieties.

As illustrations of Preparation Nos. 3 and 4, dense star polymers, e.g., amine-terminated dendrimers can be reacted with an appropriate difunctional or trifunctional compound such as an organo polyhalide, e.g., polyhaloalkaryl compounds such as 1,3,5-tris(chloromethyl)benzene or 1,4-dibromobutene, polyesters such as poly(methyl acrylate) or a chloropolyether such as polyepichlorohydrin; or polyisocyanate or polyisothiocyanate such as toluene diisocyanate, methylene diphenylene diisocyanate and polymers thereof (so-called MDI and polymeric MDI) and other aromatic polyisocyanates, aliphatic polyisocyanates and corresponding polyisothiocyanates, to form a poly(dendrimer) or bridged dendrimer having a plurality of dendrimers linked together through the residues of the polyhalide, polyester, polyether, or polyisocyanate. Dendrimer bridging also results when hydroxyl-terminated dendrimer is mixed with stoichiometric amounts of acid-terminated dendrimer under esterification conditions or when hydroxyl-terminated dendrimers are subjected to ether forming conditions.

In Preparation No. 5, dendrimers $D^1$ and $D^2$ having electrophilic terminal groups are contacted with a third dendrimer $D^3$ having nucleophilic terminal groups to yield a bridged dense star polymer or dendrimer of Formula V. For example, dendrimers having ester-terminated groups can be contacted with di- or multi-substituted polyamines or polyols to covalently bridge the dendrimers. The bridged dendrimer of Formula V can be polymerized further to yield even larger bridged dense star polymers or dendrimers.

In Preparation No. 6, a dendrimer having at least one olefinic terminal group (OT) is contacted with a second dendrimer having at least one initiator (IT) (copolymerizable) terminal group to yield a bridged dense star polymer or dendrimer of Formula VI. The bridged dense star polymer or dendrimer of Formula VI can be polymerized further to yield even larger bridged dense star polymers or dendrimers.

In Preparation No. 7, a dendrimer having an olefinic terminal group and dendrimer having an initiator (IT) (copolymerizable) terminal group are contacted with a copolymerizable monomer to form a bridged dense star polymer or dendrimer of Formula VII. The bridged dendrimer of Formula VII can be polymerized further to yield even larger bridged dense star polymers.

In another preparation, dense star polymers having nucleophilic, electrophilic, olefinic or initiator terminal groups can be heated to temperatures effective to effect covalent bridging among the dense star polymers. For example, heating amine-terminated polyamidoamines (PAMAM) dendrimers at temperatures between about 150° C.-200° C. for an effective time will transaminate the amine terminal groups, forming the covalent bridging between dendrimers. A representative example of this preparation is provided below.

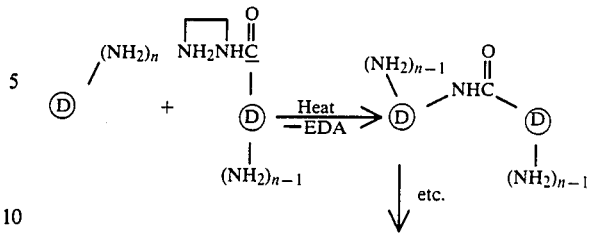

In yet another preparation, the covalently bridged dense star polymers or dendrimers can be prepared by employing less than the statistical excess of a coreactant such as ethylenediamine (EDA) used in preparing the monodispersed (nonbridged) dense star or dendrimer.

As indicated hereinbefore, in addition to the simplified situation where only two dense star polymers or dendrimers starting materials are covalently bridged, bridged dense star polymer or dendrimer can be further bridged, i.e., polymerized together to form higher bridged dense star polymers or dendrimers of a multitudinous variety of shapes and sizes.

The following diagram represents a higher bridged dense star polymer or dendrimer whose dense star polymers or dendrimers are bridged linearly. For purposes of illustration, each circle represents a dendrimer specie and the lines connecting the circles represent the bridges between the dendrimers.

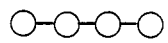

In the diagram below, the higher bridged dense star polymer or dendrimer whose dense star polymers or dendrimers are bridged in a "starburst" or radially expanding manner.

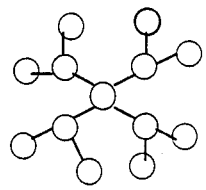

Such higher bridged dense star polymers and dendrimers can also be made from dense star polymers and dendrimers covalently bridged in a concentric or macrocyclic manner:

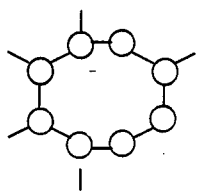

Such higher bridged dense star polymers or dendrimers can also be made from dense star polymers and dendrimers covalently bridged in rod-like structures:

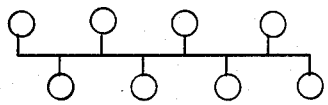

A dense star polymer or dendrimer "seed" possessing electrophilic terminal groups, i.e., esters as described in Preparation No. 3, supra, can be contacted with a plurality or excess of dense star polymers or dendrimers possessing nucleophilic terminal groups, i.e., amines. The excess dendrimers with nucleophilic terminal groups "coat" the dense star or dendrimer "seed", analogous to rolling a candy or pastry (seed) in flour (co-reactant coating). For example, if the seed has electrophilic terminal groups, the coating will have nucleophilic terminal groups. Conversely, if the seed has nucleophilic terminal groups, the coating will have electrophilic terminal groups. See, for example, Preparation No. 5. Such an enhanced bridged dense star polymer or dendrimer is illustrated as follows.

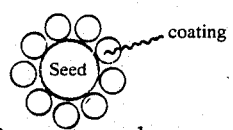

Dense star polymers whose dendrimers are covalently bridged can advantageously be constructed to possess cavitations or voids in highly bridged aggregates.

These bridged aggregates or lattices can still retain further reactivity through reactive terminal groups not used in the bridging. In addition, these dendrimer bridging reactions can be performed as to yield films, gels, beads or other fabricated shapes which possess cavitations or voids which are based on the "packing efficiency" of the dense star polymers and dendrimers being covalently bridged.

The block diagrams below schematically illustrate how the cavity size and shapes can be designed based on the covalent bridging of selected dendrimers.

|  | I<br>50 × 50 Å | II<br>50 × 60-90 Å | III<br>50 × 100 Å |
| --- | --- | --- | --- |
| Cavity Dimensions: | regular hexagonal | slightly elongated hexagonal | fully elongated octagonal |

The cavity sizes can be controlled to a large degree by the choice of dendrimer size employed. Bridging dense star polymers and dendrimers having large diameters will lead to aggregates having correspondingly large cavity sizes. Conversely, bridging dense star polymers and dendrimers having small diameters will result in aggregates having small cavity sizes. For example, based on (CPK) dimensions for various $NH_3$ core-derived dendrimers and assuming the dendrimers will hexagonally pack (see Table I), bridged dendrimer aggregates having cavity sizes ranging from Generation=1.0 (22×22-44 Å) to Generation=7.0 (126×252 Å) can be prepared.

These cavity dimensions combined with various organic moieties can serve as size selective lattices/matrices for physical separation of, modification of and catalysis reactions of a wide variety of valuable bioparticles possessing microdimensions similar to these cavities.

Conditions used to prepare the bridged dense star polymers and the bridged dendrimers of the present invention are prepared under conditions similar to those used in preparing the dense star polymers, as taught in U.S. Pat. Nos. 4,587,329; 4,568,737 and 4,507,466 whose preparative teachings are incorporated herein by reference. Dense star polymers or dendrimer starting materials having the requisite reactive nucleophilic, electrophilic, olefinic or initiator terminal groups can be contacted at temperatures ranging from −10° C. to about 250° C., preferably from ambient to about 150° C. The dense star polymers or dendrimer starting materials can be contacted at autogenous pressures, although pressures less than or greater than autogenous can be employed. The dense star polymers or dendrimer starting materials can be stirred or not stirred during the contacting, although stirring is preferred. The resultant covalently bridged dense star polymers or dendrimers can be recovered after covalent bridging of the dense star polymer or dendrimer starting materials by conventional procedures, such as solvent extraction, crystallization, precipitation, evaporation, and filtration. The molar ratios of dense star polymer or dendrimer starting materials can vary greatly, depending upon the degree of covalent bridging desired, the desired geometric configuration of the bridged dense star polymer or dendrimer, and the desired degree of activity of the residual terminal groups on the bridged dense star polymer or dendrimer. The requisite molar ratio of reactants can be established by one of ordinary skill.

The following working examples are given to illustrate the disclosed dense star polymers and bridged dense star polymers as well as method for their preparation. In such working examples, all parts and percentages are by weight unless otherwise indicated.

EXAMPLE 1

Polyamidoamine Dendrimer-Excess Reactant Method

A. Preparation of Core Adduct

To a one-liter, 3-neck flask equipped with stirrer, condenser, thermowell, and containing ammonia (8.7 g, 0.58 mole) dissolved in 102.2 g of methanol is added methyl acrylate (296.5 g, 3.45 moles) at room temperature with stirring over a 6-hour period. The mixture is allowed to stand at room temperture for 48 hours at which point excess methyl acrylate is removed by vacuum distillation (1 mm Hg at 22° C.) yielding 156 g of residue. This residue is analyzed by size exclusion chromatography ($C_{13}$ NMR) and liquid chromatography. This analysis indicates the coreactant adduct to be the Michael's addition product of 1 mole of ammonia and 3 moles of methyl acrylate at a 97.8 percent yield.

B. Preparation of First Generation Adduct

To ethylenediamine (505.8 g, 8.43 moles) dissolved in 215.4 g of methanol in a 3-liter reaction flask equipped with stirrer, condenser and thermowell, is added the aforementioned ammonia/methyl acrylate adduct (28.1 g, 0.1022 mole), and the reaction mixture is allowed to stand at room temperature for 55 hours. The resulting mixture (747.6 g) is subjected to vacuum distillation to remove excess ethylenediamine and methanol at 2 mm Hg and 72° C. The residue (35.4 g) is analyzed by size exclusion chromatography and other suitable analytical techniques. The analyses indicate that essentially all of the ester moieties of the ammonia/methyl acrylate adduct had been converted to amides in the form of a compound represented by the following structural formula:

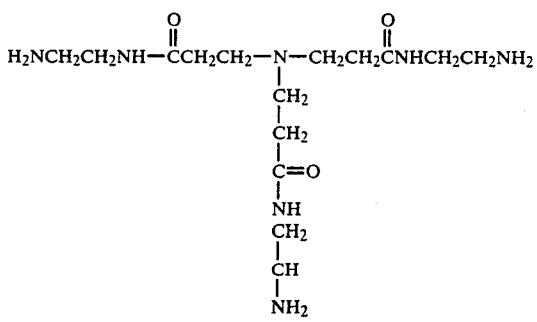

thus indicating a yield of 98.6 percent.

C. Preparation of Second Generation Polyester Dendrimer

To methyl acrylate (93.2 g, 1.084 moles) in a one-liter flask equipped with condenser, stirrer and thermowell, and heated to 32° C. is added the aforementioned first generation adduct (18 g, 0.0501 mole) dissolved in 58.1 g of methanol over 1.5 hours. The resulting mixture is maintained at 32° C. for an additional 5 hours and allowed to stand an additional 18 hours at room temperature. The reaction mixture (165.7 g) is stripped of methanol and excess methyl acrylate by vacuum distillation (2 mm Hg and 50° C.) to produce 43.1 g of residue. Analysis by suitable techniques indicates the product to be a second generation polyester dendrimer represented by the following formula:

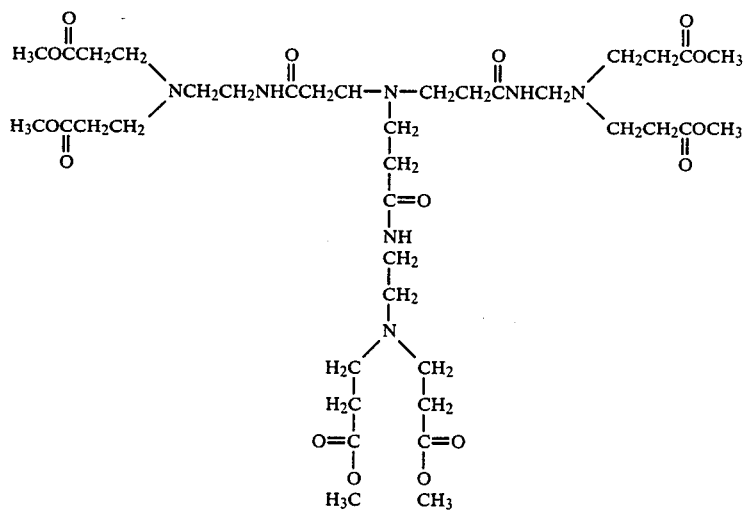

in 98.4 percent yield.

D. Preparation of Second Generation Polyamine Dendrimer

To ethylenediamine (328.8 g, 5.48 moles) dissolved in 210.2 g of methanol at room temperature in the aforementioned flask is added with stirring the second generation polyester dendrimer (34.9 g, 0.0398 mole) dissolved in 45.3 g of methanol. The resulting mixture is allowed to stand for 66 hours at room temperature at which time excess ethylenediamine and methanol is stripped from the product by vacuum distillation (2 mm Hg at 72° C.) to yield 41.1 g (99.0 percent yield) of product. This product is determined by size exclusion chromatography to be the second generation polyamine of the aforementioned polyester dendrimer.

E. Preparation of Third Generation Polyester Dendrimer

To methyl acrylate (65.1 g, 0.757 mole) is added the aforementioned second generation polyamine dendrimer (28.4 g, 0.0272 mole) dissolved in 84.6 g of methanol over a period of 1 hour and 15 minutes. The resulting mixture is allowed to stand for 18 hours at 25° C. after which time excess methyl acrylate and methanol are removed by vacuum distillation (2 mm Hg at 50° C.) to yield 56.3 g (100.0 percent yield) of product residue. Analysis of this residue by suitable analytical techniques indicate that it is a third generation polyester dendrimer having 3 core branches with 4 terminal ester moieties per core branch thereby providing 12 terminal ester moieties per dendrimer molecule.

F. Preparation of Third Generation Polyamine Dendrimer

To ethylenediamine (437.6 g, 7.29 moles) dissolved in 192 g of methanol is added the aforementioned third generation polyester dendrimer (44.9 g, 0.0216 mole) dissolved in 69.7 g of methanol. The addition occurs over a period of 48 hours at 25° C. with stirring. The resulting reaction mixture is then allowed to stand for 19 hours at 25° C. after which time excess methanol and ethylenediamine are removed by vacuum distillation (2 mm Hg at 72° C.) to yield 51.2 g of residual product. Analysis of this residue indicates a yield of 85.3 percent of a third generation polyamine dendrimer having 3 core branches with 4 terminal primary amine moieties per core branch, thereby providing 12 terminal primary amine moieties per molecule of dendrimer. This dendrimer is calculated to have a molecular volume of 50,000 to 97,000 cubic A and a density of a terminal amine moiety of 1 to 3($\times 10^{-4}$) moieties/cubic Å.

G. Preparation of Bridged Dendrimer

Following the general procedure of Example 3, a bridged dendrimer of the third generation dendrimer of Part F is prepared and evaluated in the demulsification method set forth in Example 4.

EXAMPLE 2

Bridged Polyamine Dendrimer

Monodispersed dendrimers 0.5 Generation from an ammonia ($NH_3$) core are prepared by exhaustive alkylation (Michael addition) of ammonia with methyl acrylate. The monodispersed dendrimers are contacted with ethylenediamine (EDA) in a series of molar ratios ranging from 10:1 to 2:1 (EDA:dendrimer).

The reaction product from each contacting is vacuum stripped of excess ethylenediamine and methanol, the by-product of the reaction. The products are then analyzed by size exclusion chromatography using Spherogel® TSK 2000 and 3000 PW columns available from Beckman Instruments, Inc., Berkeley, Calif. The columns are connected in series and each is 30 cm in length. The eluent is 0.05M $K_2HPO_4$ pH adjusted to 11 with 50 weight percent NaOH. Injections are 0.1 ml of 0.5 percent solution and the flow rate is 1 ml/min. Differential refractive index detection is used to monitor the dense star polymer elution. This chromatographic method is capable of resolving the first generation dendrimer from the various bridged dendrimer species which elute earlier. Table II shows the purity of the product from each contacting expressed as weight percent first generation (1 G) dendrimer in the product.

TABLE II

| Mole Ratio EDA: 0.5 G Dendrimer | Weight Percent 1 G Dendrimer in product |
| --- | --- |
| 10:1 | 76 |
| 7:1 | 62 |
| 5:1 | 44 |
| 3:1 | 19 |
| 2:1 | Sample Gelled |

Table II clearly shows that this process yields a smaller and smaller portion of the desired product as the ratio of EDA to the starting dendrimer is decreased. Furthermore, the chromatograms show that as this ratio is decreased, the product contains bridged dendrimer of higher and higher molecular weight until at the 2:1 ratio the product is a gel.

EXAMPLE 3

Bridged Dendrimer by Reaction of a Polyamine Dendrimer with a Polyester Dendrimer Into a vial is charged the dendrimer of Part E of Example 1 (0.28 g) and the dendrimer of Part F of Example 1 (0.32 g), to give a colloidal, opaque paste. Adding 2 ml of deuterated chloroform ($CDCl_3$) causes a portion of the dendrimer mixture to dissolve. Adding ≅0.5 ml of MeOH obtains a totally homogeneous solution. A film (≅1 ml) of this reaction mixture is cast on (a) an infrared salt plate and (b) on Teflon® coated plate. Teflon® is a trademark of E. I. DuPont DeNemours & Co., Wilmington, DE 19898. These samples are placed in an oven at 100° C. and are monitored by infrared analysis over a period of 65 hours. Ratios of ester (1730 $cm^{-1}$) to amide (1652 $cm^{-1}$) bands are determined and are as shown in Table III.

TABLE III

| Time Elapsed (hours) | % Ester (1730 $cm^{-1}$) | % Amide (1652 $cm^{-1}$) |
| --- | --- | --- |
| 0.00 | 42 | 57 |
| 0.83 | 39 | 61 |
| 21.00 | 32 | 68 |
| 30.50 | 30 | 70 |
| 47.00 | 27 | 73 |
| 65.00 | 23 | 77 |

The ester band (1730 $cm^{-1}$) diminishes dramatically (≅10 percent; ≅0.5 percent/hour) during the first 21 hours (100°) with concurrent formation of amide band (1652 $cm^{-1}$). After that time, loss of ester levels out at ≅0.2 percent/hour and continues at that rate after 65 hours/100°. The film is removed from the TFE plate after 30 hours, dissolved/slurried in water and filtered through an XM-300 (pore size ≅200 Å having ability to retain polymer of $\overline{M}_n$ of 300,000 or more) obtained from Amicon Corporation, Lexington, Mass. The filterate is refiltered through an XM-100 (pore size ≅50 Å having ability to retain polymer of $\overline{M}_n$ of 50,000 or more) and the retained sample portion is diluted with $H_2O$ and examined by electron microscopy. Using the method of Richardson and Quayle, the sample is sprayed on a carbon-coated (50 Å), beryllium grid and examined by a Philips 400 TEM microscope. Electron micrographs show the major population is made of "starburst polymer" aggregates with cross-sectional dimensions of ≅50–600 Å.

EXAMPLE 4

Demulsification Method

To 100 ml of an oil-in-water emulsion containing about 5 percent of crude oil having a specific gravity of ≅0.98 g/ml is added one part per million based on the emulsion of the bridged dendrimer of Example 1 and Example 3. Each emulsion is then shaken for 3 minutes to effectively disperse the dendrimer into the emulsion. Each emulsion is allowed to stand for 10 minutes and visually evaluated. After 10 minutes, each emulsion appears to be completely resolved into two phases having a distinct interface wherein the aqueous phase is essentially transparent.

Following the foregoing procedure except substituting a quaternized form of the foregoing bridged dendrimer for the bridged dendrimer, the emulsion is similarly resolved using 0.5 ppm and 1 ppm of the quaternized form. This quaternized form is prepared by reacting the 32.42 g (0.01 mole) of the dendrimer in 100 ml of methanol with 24.32 g (0.16 mole) of 2-hydroxy-3-chloropropyl trimethyl ammonium chloride in 30 ml of water at 50° C. for about 12 hours.

EXAMPLE 5

Polyalkyleneopolyamine Dendrimer Protected Reactant Method

A. Preparation of First Generation Star Polymer

A 35.5 percent solution of $H_2SO_4$ in $H_2O$ is made by dissolving 191.1 g ($H_2SO_4$, 98 percent) in 347 g of deionized water. To this solution, in a 500-ml 3-necked flask equipped with stirrer, condenser and addition funnel, is added neat diethylenetriamine (154.5 g, 1.5 moles), while stirring and cooling (ice) at such a rate that the temperature does not exceed 65° C.–70° C. After this addition, aziridine (21.5 g, 0.5 mole) is added dropwise while stirring and cooling (<50°) over a period of 0.5 hour. The resulting bright yellow, orange reaction mixture is then stirred while heating at 40° C.–50° C. for 6 hours. To this crude reaction mixture is added 240 g (6.0 moles) of NaOH in portions while stirring. An exotherm is noted which gives a brown-yellow layer which separates from a lower, salt-containing, aqueous layer. The organic (top) layer is separated and found to weigh 287.3 g and contains a substantial amount of water. Solid sodium hydroxide (75 g) is added to this fraction causing a brown layer (top) to separate, which weighs 174.3 g (99 percent of theory). Distillation through a ½×8 inch Vigreux column gives a light yellow liquid, b.p. 123° C.–128° C. at 3 mm Hg, which is determined to be the adduct of 1 mole of aziridine and 1 mole of diethylenetriamine represented by the formula:

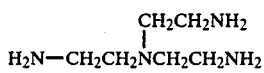

First Generation Star Polymer

B. Preparation of N-(Tosyl)Aziridine p-Toluene sulfonyl chloride (38.0 g, 0.2 mole) is dissolved in 100 ml of diethyl ether in a 250-ml 3-necked flask equipped with stirrer, condenser and addition funnel. To this stirred solution is added triethylamine (20.2 g, 0.2 mole) in a dropwise manner. While stirring and maintaining the reaction temperature at 10° C.–20° C. with an ice-bath, a solution of aziridine (8.6 g, 0.2 mole) in 75 ml of diethyl ether is added dropwise over a period of 15–30 minutes. A thick white precipitate forms. Additional ether (100–150 ml) may be added to facilitate stirring. The reaction mixture is stirred for an additional hour at room temperature and filtered. Washing the filter cake with 2×100 ml portions of ether gives essentially a quantitative yield of $Et_3N \cdot HCl$. Removal of solvent from the filtrate gives light cream colored crystals which weigh 25.0 g (62 percent yield). Recrystallization from $Et_2O$/hexane gives white crystals, m.p. 60° C.–62° C. which are determined by nuclear magnetic resonance to be N-(tosyl)aziridine represented by the formula:

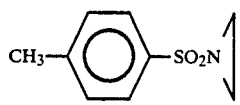

C. Preparation of Protected Polyamine Dendrimer (Second Generation)

The first generation polyamine of Part A (3.5 g, 0.024 mole) and N-tosyl (Tos) aziridine (38.55 g, 0.145 mole) are placed in 50 ml of 95 percent ethanol in a 100-ml vessel equipped with a stirrer. The mixture is stirred at room temperature. Over a period of 2 hours the tosyl aziridine slowly dissolves giving a colorless homogeneous solution after which a white precipitate forms which makes stirring difficult. Additional stirring (1 hour) leads to a solid mass. After adding another 50 ml of ethanol and stirring overnight (25° C.), the white solids are isolated by filtration, washed with 2×100 ml EtOH and 2×150 ml $Et_2O$ and dried by suction. Weight of white solids product is 27.7 g (87 percent). Nuclear magnetic resonance spectral analysis confirms the tosyl hexa-adduct represented by the formula:

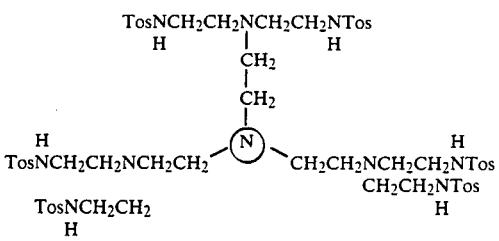

D. Removal of Protecting Tosyl Groups

The protected polyamine dendrimer of Part C (27.7 g, 0.021 mole) is mixed with 130 ml of degassed concentrated sulfuric acid (98 percent) under nitrogen in a one-liter round-bottom flask equipped with stirrer, nitrogen purge and reflux condenser. The mixture is heated at 130° C. for 6 hours. The reaction is complete after 6–10 hours as determined by a test which involves basifying the sample with 10 percent NaOH. The absence of cloudiness at alkaline pH indicates complete reaction. After cooling the reaction mixture to 0° C., diethyl ether (600 ml) is added in small portions to maintain the temperature $\leq 10°$ C. The resulting white, hygroscopic precipitate is isolated by filtration and then dissolved in water. This water solution is basified to pH $\geq 10$ with 20 percent KOH. Removal of the water yields a mixture of oily product and solid $K_2SO_4$. Extraction with methanol (200 ml) and filtration gives the product as a flowable oil, after methanol removal. Upon heating under high vacuum, the remaining volatiles are removed to give a yellow-orange syrup. Nuclear magnetic resonance spectral analysis confirms the aforementioned syrup to be a second generation polyamine dendrimer represented by the formula:

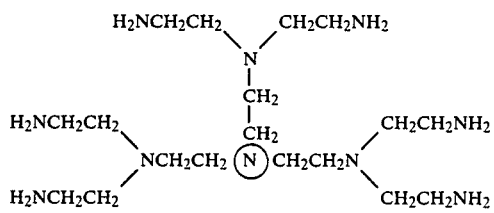

Polyamine Dendrimer (Second Generation)

E. Bridging of Dendrimer

Following the procedure of Example 3, a bridged dendrimer is prepared and found to be a useful demulsifier in the procedure described in Example 4.

EXAMPLE 6

Use of Bridged Dendrimer from Protected Reactant Method

A. Transition Method Ion Control

A 0.1-g portion of the bridged dendrimer of Example 5 dissolved in 5 ml of deionized water is added dropwise under ambient conditions to a solution of 0.1 g of copper sulfate in 3 ml of deionized water. A deep blue color accompanied by the formation of a heavy precipitate (floc) is observed. The precipitate is readily removed by centrifugation, then demonstrating the control (removal) of Cu (II) ion by formation of complex betweeen Cu (II) ion and dendrimer.

B. Heavy Metal Ion Control

A 0.1-g portion of the bridged dendrimer of Example 5 dissolved in 5 ml of deionized water is added dropwise under ambient conditions to a solution of 0.1 g of uranyl nitrate ($UO_2(NO_3)_2 6H_2O$) dissolved in 3 ml of deionized water. A brilliant yellow color accompanied by the formation of a heavy precipitate (floc) is observed. The resulting complex (precipitate) is isolated by centrifugation, thus demonstrating the ability of dendrimer to control (remove) U (VI) ion formation of complex between the dendrimer and the U (VI) ion.

What is claimed is:

1. A bridged dense star polymer comprising at least two dense star polymer molecules connected by a covalent linkage, such dense star polymer molecules which prior to bridging have at least one core branch emanating from a core, each core branch having at least one terminal group provided that (1) the ratio of terminal groups to the branches emanating from the core is 2:1 or greater, (2) the density of terminal groups in the dense star polymer is at least 1.5 times that of an extended conventional star polymer having similar core and monomeric moieties and a comparable molecular weight and number of core branches wherein each of such branches of the extended conventional star polymer bears only one terminal group, (3) a molecular volume that is equal to or less than 80 percent of the molecular volume of said extended conventional star polymer, and (4) the two-dimensional molecular diameter of the dense star polymer is in the range from about 12 to about 2000 Angstroms.

2. The bridged dense star polymer of claim 1 wherein the dense star polymer molecules have (1) at least 2 core branches per core, (2) a terminal group density at least 5 times that of the corresponding extended conventional star polymer, (3) a molecular volume that is equal to or less than 60 percent of the volume of the extended conventional star polymer, and (4) the two-dimensional molecular diameter of the dense star polymer is in the range from about 25 to about 500 Angstroms.

3. The bridged polymer of claim 1 which has at least two dendrimer molecules having a polyvalent core that is covalently bonded to at least 1 ordered dendritic branch which extends to two generations such that each dendritic branch has at least four terminal groups and a symmetrical structure.

4. The bridged polymer of claim 1 wherein the core is derived from a nucleophilic compound.

5. The bridged polymer of claim 4 wherein the nucleophilic compound is an amine having a plurality of amine hydrogens.

6. The bridged polymer of claim 1 wherein the dense star polymer molecules have at least 3 core branches per core.

7. The bridged dense star polymer of claim 3 wherein the dense star polymer molecules have at least 3 core branches per core.

8. A bridged dense star polymer which comprises at least two dendrimer molecules which are covalently bonded together and which molecules are represented by the formula:

$$\left( (I)(Z^c)_{N_c} \right) \left\{ (X^i Y^i(Z^i)_{N_i}) N_c \pi N^n \bigg|_{n \text{ is } 1}^{i-1} \right\} (X^t Y^t(Z)^t_{N_t}) N_c \pi N^m \bigg|_{n \text{ is } 1}^{t-1}$$

where $i$ is $1$ to $t - 1$ wherein (I) is a polyfunctional core, $Z^c$ is a functional group bonded to the core and a X group of the first generation, $N_c$ is the number of functional group bonded to the core, $X^i$ is a monofunctional tail of a repeating unit $Y^i$ of the i generation which is bonded to $Y^i$ and a Z group of the $i-1$ generation, $Z^i$ is a functional group bonded to $Y^i$ and a X group of the $i+1$ generation, $N^i$ is a number of at least 2 which corresponds to the multiplicity of the polyfunctional head of $Y^i$, $\pi$ is the product function, $N^{i-1}$ is a number of at least 2 which corresponds to the multiplicity of the polyfunctional head of $Y^{i-1}$ wherein $Y^{i-1}$ is a repeating unit of the $Y^{i-1}$ generation, $X^t$ is the monofunctional tail of a repeating unit $Y^t$ of the terminal generation, $Z^t$ is a terminating group bonded to $Y^t$, $N^t$ is zero or a number which corresponds to the number of $Z^t$ groups bonded to one $Y^t$ group, i represents a number of a particular generation in a series from 1 to a number from 1 to $t-1$, provided that (1) all $X^i Y^i(Z^i)_{N_i}$ are the same within a generation and are the same or different in different generations and (2) all $X^t Y^t(Z^t)_{N_t}$ of the terminal generation are the same.

9. The bridged dense star polymer of claim 8 wherein t is 2 or more and $N^t$ is at least one.

10. The bridged dense star polymer of claim 8 wherein t is 3 or more and $N_t$ is at least two.

11. The bridged polymer of claim 1 wherein the dendritic branches contain ether or thioether linkages.

12. The bridged polymer of claim 8 wherein the core is derived from a nucleophilic compound and the branches contain polyether or polythioether moieties wherein the terminal groups are primary amine groups.

13. The bridged polymer of claim 8 wherein the core is derived from a core compound having a plurality of halogens each capable of reacting with an alcohol moiety.

14. The bridged polymer of claim 8 which is represented by the formula:

$$\left\{ ((I)(Z)^c_{N_c}) \left\{ (X^i Y^i(z)^i_{N_i}) N_c \pi N^n \bigg|_{n \text{ is } 1}^{i-1} \right\} (X^t Y^t(Z)^t_{N_t}) N_c \pi N^m \bigg|_{n \text{ is } 1}^{t-1} - L (X^t Y^t(\Omega)^t)_L \right\}_V$$

where $i$ is to $t - 1$ $\Omega$ is the linking group formed from $Z^t$

L is the number of terminal groups ($Z^t$) converted to bridging links ($\Omega$)

V is the degree of polymerization which is 2 or greater.

15. The bridged dense star polymer of claim 1 wherein the bridge is formed by contacting a dendrimer having at least one nucleophilic terminal group with at least one other dendrimer having at least one electrophilic terminal group to form said covalent bridge between said terminal groups.

16. The bridged dense star polymer of claim 15 wherein the nucleophilic terminal group is amino, mercapto, carboxyl, hydroxyl or malonyl.

17. The bridged dense star polymer of claim 15 wherein the electrophilic terminal group is carboxy ester, Michael receptor activated olefin, oxirane, aziridinyl, anhydride, allylic, benzylic halide, acid halide, ammonium salt or sulfonium salt.

18. The bridged dense star polymer of claim 1 wherein the dense star polymers are covalently bridged in a concentric manner.

19. The bridged dense star polymers of claim 1 wherein the dense star polymer molecules are covalently bridged in a rod-like structure.

20. The bridged dense star polymer of claim 1 wherein a first dense star polymer is coated with a plurality of dense star polymers covalently bridged to said first dense star polymer.

21. The bridged dense star polymer of claim 1 wherein a plurality of dense star polymer molecules are covalently bridged into a lattice or matrix having a cavity therein.

22. The bridged dense star polymer of claim 1 wherein the core of the dense star polymer is derived from an electrophilic compound.

23. The bridged dense star polymer of claim 19 wherein the carboxy ester is tosylate, mesylate or triflate.

24. The bridged dense star polymer of claim 1 wherein the bridge is formed by contacting a dendrimer having at least one olefinic terminal group with at least one dendrimer having a corresponding initiator terminal group to form said bridge between said terminal groups.

25. The bridged dense star polymer of claim 24 wherein the olefinic terminal group is acrylate, acrylamido, styryl, methacrylamido, methacrylate, allylic, cinammate or itaconate.

26. The bridged dense star polymer of claim 1 wherein the bridge is formed by contacting a dendrimer having at least one terminal group which is nucleophilic or olefinic with at least one dendrimer having at least one terminal group which is electrophilic or an initiator wherein the contacting is performed in the presence of a copolymerizable monomer to form a bridge between said terminal group of each dendrimer through said copolymerizable monomer.

27. The bridged dense star polymer of claim 26 wherein the copolymerizable monomer is styrene, alkyl acrylate, alkyl methacrylate, acrylamide, n-alkylamide acylamides, alkenyl oxazoline, vinyl halide, vinylidene halide, itaconate, allylic amines or allylic halide.

28. The bridged dense star polymer of claim 1 wherein the bridge is formed by heating a plurality of dense star polymers having nucleophilic, electrophilic, olefinic or initiator terminal groups to temperatures effective to effect covalent bridging among the dense star polymers.

29. The bridged dense star polymer of claim 1 wherein the covalent bridge is formed by heating a plurality of dendrimers having nucleophilic, electrophilic, olefinic or initiator terminal groups to temperatures effective to effect covalent bridging among the dense star polymers.

30. The bridged dense star polymer of claim 1 wherein the covalent bridge is formed by employing less than the statistical excess of a coreactant needed to prepare a monodispersed dense star polymer.

31. The bridged dense star polymer of claim 1 wherein the dense star polymer molecules are covalently bridged linearly.

32. The bridged dense star polymers of claim 1 wherein the dense star polymer molecules are covalently bridged in a radially expanding manner.

* * * * *

UNITED STATES PATENT AND TRADEMARK OFFICE
CERTIFICATE OF CORRECTION

PATENT NO. : 4,737,550

DATED : April 12, 1988

INVENTOR(S) : Donald A. Tomalia

It is certified that error appears in the above-identified patent and that said Letters Patent is hereby corrected as shown below:

Column 4, line 23, the word "purpose" should be -- purposes --.

Column 8, in the formula shown between lines 5-30, "(Zi)" contained in the innermost set of brackets should correctly appear as -- $(Z)^i$ --.

Column 8, in the formula shown between lines 5-30, the words "where i is to t - 1" should be -- where i is 1 to t - 1 --.

Column 8, line 49, the word "as" should be -- is --.

Column 8, in the diagram shown between lines 51-62, the "I" in the core of the drawing should appear as --(I)--.

Column 10, in the formula shown on line 68, "I" should correctly appear as --(I)--.

Column 11, in the formula shown on line 53, "T(U) V m" should correctly appear as -- T(U)(V) m --.

Column 11, in the formula shown on line 57 "T)U(V) m]n" should correctly appear as -- T+U(V) m]n --.

UNITED STATES PATENT AND TRADEMARK OFFICE
CERTIFICATE OF CORRECTION

PATENT NO. : 4,737,550

DATED : April 12, 1988

INVENTOR(S) : Donald A. Tomalia

It is certified that error appears in the above-identified patent and that said Letters Patent is hereby corrected as shown below:

Column 11, in the formula shown on line 63, "$W[(X'-T')UV_mT'-$" should correctly appear as -- $W[(X'-T')\}UV_mT'-$ --.

Column 12, line 17, "hydroxyethyaminoethylamine" should read -- hydroxyethylaminoethylamine --.

Column 15, in the formula on line 7, "S" should be preceded by a dash, to correctly appear as -- -S- --.

Column 15, in the formula #2 under "Reaction Mechanism", the circle around "ET" has been omitted. It should correctly appear as --(ET)--.

Column 16, in formula #2 under "Dense Star Polymer Product", a single wavy line should depend from D3. It should correctly appear as --(D3)--.

Column 19, the diagram between lines 40-53 is drawn incorrectly, it should appear as follows

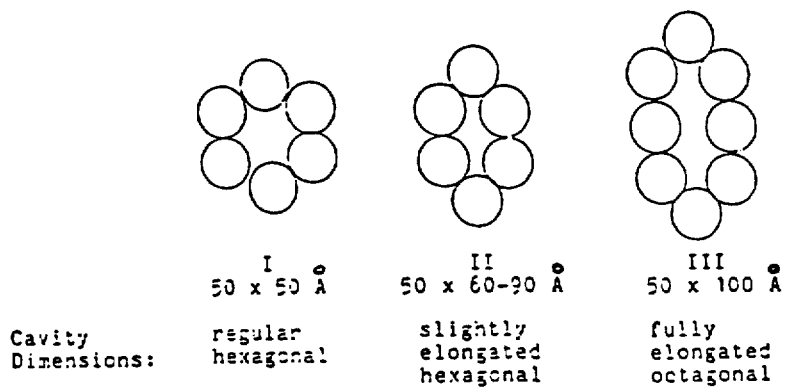

UNITED STATES PATENT AND TRADEMARK OFFICE
CERTIFICATE OF CORRECTION

PATENT NO. : 4,737,550

DATED : April 12, 1988

INVENTOR(S) : Donald A. Tomalia

It is certified that error appears in the above-identified patent and that said Letters Patent is hereby corrected as shown below:

Column 20, line 50, the word "temperture" should correctly appear as -- temperature --.

Column 24, line 56, the word "Polyalkyleneopolyamine" should correctly appear as -- Polyalkylenepolyamine --.

Column 26, line 56, the word "Method" should be -- Metal --.

Column 28, in the formula on line 4, "(Z)t" should correctly appear as --$(Z^t)$--

Column 28, in the formula on lines 46-52, the words "where i is to t - 1" should be -- where i is 1 to t - 1 --.

Signed and Sealed this

Fourteenth Day of June, 1994

BRUCE LEHMAN

*Attest:*

*Attesting Officer*     Commissioner of Patents and Trademarks